(12) United States Patent
Hamagami et al.

(10) Patent No.: US 11,410,251 B2
(45) Date of Patent: Aug. 9, 2022

(54) INFORMATION PROCESSING SYSTEM, PROGRAM, AND CONTROL METHOD

(71) Applicant: TOYOTA JIDOSHA KABUSHIKI KAISHA, Toyota (JP)

(72) Inventors: Kana Hamagami, Nissin (JP); Takuya Maekawa, Nissin (JP); Yosuke Nakayama, Owariasahi (JP); Akitoshi Jikumaru, Nissin (JP); Tae Sugimura, Miyoshi (JP); Takao Hishikawa, Nagoya (JP); Shinichi Adachi, Takahama (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 37 days.

(21) Appl. No.: 16/783,324

(22) Filed: Feb. 6, 2020

(65) Prior Publication Data
US 2020/0273121 A1 Aug. 27, 2020

(30) Foreign Application Priority Data
Feb. 26, 2019 (JP) .............................. JP2019-033106

(51) Int. Cl.
*G06Q 50/14* (2012.01)
*G01C 21/36* (2006.01)
(Continued)

(52) U.S. Cl.
CPC ......... *G06Q 50/14* (2013.01); *G01C 21/3679* (2013.01); *G06V 20/56* (2022.01);
(Continued)

(58) Field of Classification Search
CPC ........ G06Q 50/14; G16H 50/00; G16H 50/50; G16H 50/70; G16H 20/40; G01C 21/3679;
(Continued)

(56) References Cited

U.S. PATENT DOCUMENTS

2009/0036145 A1* 2/2009 Rosenblum ............. H04W 4/02
455/456.3
2016/0170998 A1* 6/2016 Frank .................... G06F 16/337
707/748

(Continued)

FOREIGN PATENT DOCUMENTS

JP 2017-194898 A 10/2017

OTHER PUBLICATIONS

U.S. Appl. No. 16/590,561, filed Oct. 2, 2019.

*Primary Examiner* — Matthew K Kwan
(74) *Attorney, Agent, or Firm* — Oblon, McClelland, Maier & Neustadt, L.L.P.

(57) ABSTRACT

An information processing system includes a vehicle and an information processing device that acquires information acquired by the vehicle from the vehicle. The vehicle acquires information on an occupant in a passenger compartment of the vehicle, and acquires position information of the vehicle. When it is determined based on the information on the occupant that the vehicle has traveled to the vicinity of a hidden tourist attraction, the information processing device generates tourist attraction information including the position information of the vehicle at a point at which the determination has been performed.

9 Claims, 5 Drawing Sheets

(51) Int. Cl.
  *G06V 20/56* (2022.01)
  *G16H 50/00* (2018.01)
  *H04N 5/247* (2006.01)
  *B60R 11/04* (2006.01)
  *B60R 11/00* (2006.01)
  *G06V 20/59* (2022.01)

(52) U.S. Cl.
  CPC ............ *G06V 20/59* (2022.01); *G16H 50/00* (2018.01); *H04N 5/247* (2013.01); *B60R 11/04* (2013.01); *B60R 2011/0003* (2013.01); *B60R 2011/004* (2013.01)

(58) Field of Classification Search
  CPC .... G06K 9/00791; H04N 5/247; B60R 11/04; B60R 2011/0003; B60R 2011/004; B60R 16/02; G06V 20/56; G06V 20/59; G06V 40/168; G06F 16/29
  USPC .......................................................... 348/77
  See application file for complete search history.

(56) References Cited

U.S. PATENT DOCUMENTS

2017/0251163 A1* 8/2017 Ochiai ............... H04N 5/23219
2017/0350718 A1* 12/2017 Schulz .................. B60K 35/00

\* cited by examiner

FIG. 4

| POINT P | INFORMATION ON OCCUPANT | DEGREE OF EXCITEMENT OF OCCUPANT | HIDDEN TOURIST ATTRACTION | INFORMATION ON TRAVELING ENVIRONMENT | TRAVELING DIRECTION |
|---|---|---|---|---|---|
| P1 | EXPRESSION AND ACTION (VERY EXCITED) | HIGH | YES | LANDSCAPE | NORTH |
| P2 | EXPRESSION AND ACTION (SLIGHTLY EXCITED) | MIDDLE | NO | SOUNDS OF NATURE | SOUTH |
| P3 | EXPRESSION AND ACTION (COOL) | LOW | NO | SMELLS OF NATURE | EAST |
| ... | ... | ... | ... | ... | ... |

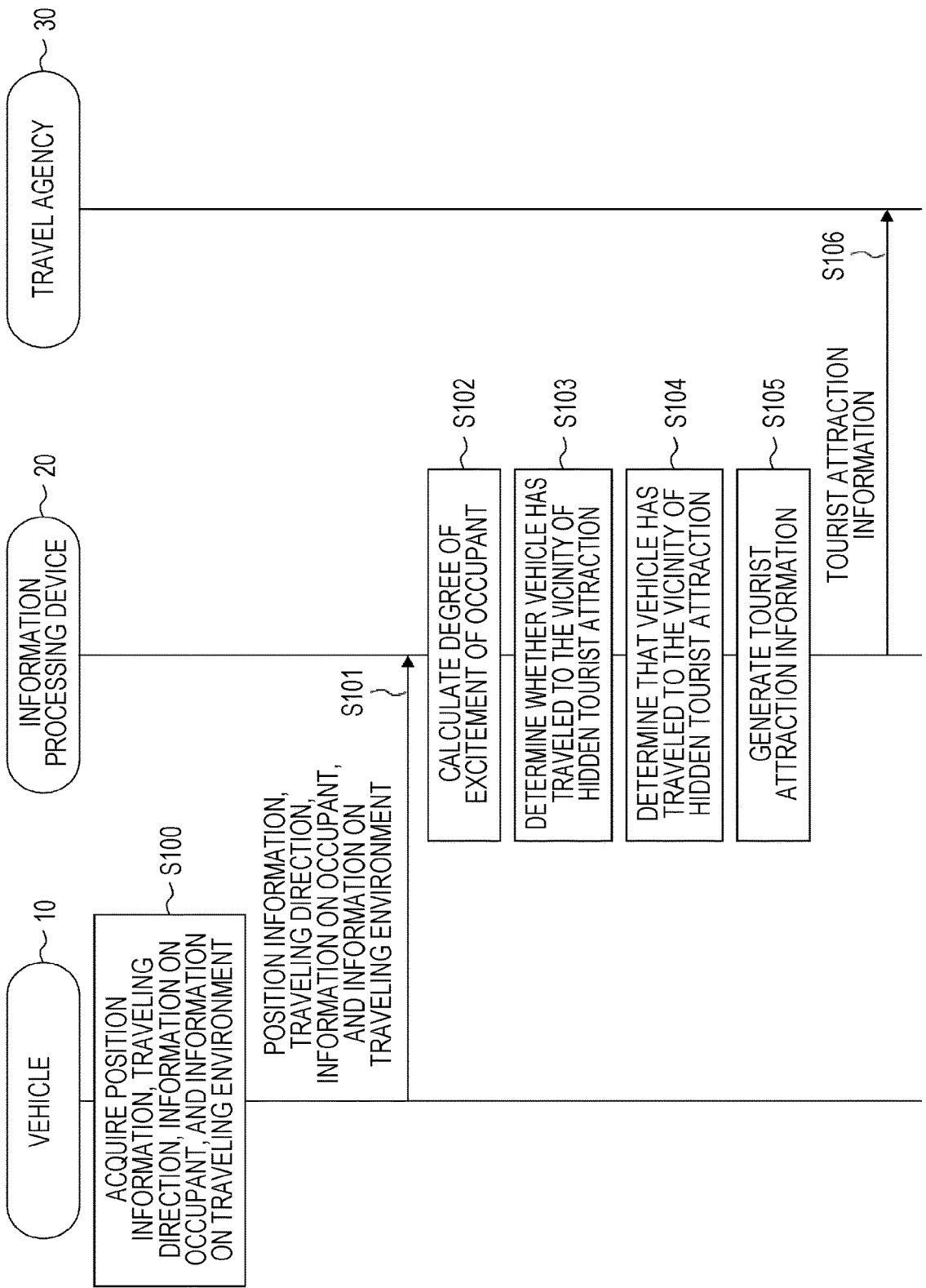

INFORMATION PROCESSING SYSTEM, PROGRAM, AND CONTROL METHOD

INCORPORATION BY REFERENCE

The disclosure of Japanese Patent Application No. 2019-033106 filed on Feb. 26, 2019 including the specification, drawings and abstract is incorporated herein by reference in its entirety.

BACKGROUND

1. Technical Field

The disclosure relates to an information processing system, a program, and a control method.

2. Description of Related Art

In the related art, a technique of performing sightseeing guidance for tourists without a tourist guide is known. For example, Japanese Patent Application Publication No. 2017-194898 (JP 2017-194898 A) discloses a sightseeing guidance system that stores determination image data including an image of a predetermined object in advance, receives imaging data from an onboard camera device, and performs output of speech based on corresponding speech data when it is determined that the object in the determination image data has been imaged.

SUMMARY

There is demand for sightseeing guidance for locations which are already widely known as tourist attractions and there is also demand for discovery of hidden tourist attractions which are not yet known as tourist attractions.

The disclosure provides an information processing system, a program, and a control method that can contribute to discovery of a hidden tourist attraction.

An information processing system according to an embodiment of the disclosure is an information processing system including a vehicle and an information processing device that acquires information acquired by the vehicle from the vehicle, wherein the vehicle acquires information on an occupant in a passenger compartment of the vehicle and acquires position information of the vehicle. When it is determined based on the information on the occupant that the vehicle has traveled to the vicinity of a hidden tourist attraction, the information processing device generates tourist attraction information including the position information of the vehicle at a point at which the determination has been performed.

A program according to an embodiment of the disclosure is a program that operates in an information processing system including a vehicle and an information processing device that acquires information acquired by the vehicle from the vehicle, the program causing the vehicle to perform: acquiring information on an occupant in a passenger compartment of the vehicle; and acquiring position information of the vehicle, and the program causing the information processing device to perform: determining whether the vehicle has traveled to the vicinity of a hidden tourist attraction based on the information on the occupant; and generating tourist attraction information including the position information of the vehicle at a point at which the determination has been performed when it is determined that the vehicle has traveled to the vicinity of a hidden tourist attraction.

A control method according to an embodiment of the disclosure is a control method in an information processing system including a vehicle and an information processing device that acquires information acquired by the vehicle from the vehicle, the control method including: causing the vehicle to acquire information on an occupant in a passenger compartment of the vehicle; causing the vehicle to acquire position information of the vehicle; causing the information processing device to determine whether the vehicle has traveled to the vicinity of a hidden tourist attraction based on the information on the occupant; and causing the information processing device to generate tourist attraction information including the position information of the vehicle at a point at which the determination has been performed when it is determined that the vehicle has traveled to the vicinity of a hidden tourist attraction.

With the information processing system, the program, and the control method according to the embodiment of the disclosure, it is possible to contribute to discovery of a hidden tourist attraction.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein:

FIG. 4 is a diagram illustrating a specific example of determination information including tourist attraction information which is stored in a storage unit of the information processing device; and FIG. 5 is a sequence diagram illustrating an example of a flow of operations in the information processing system.

DETAILED DESCRIPTION OF EMBODIMENTS

Figure 1:
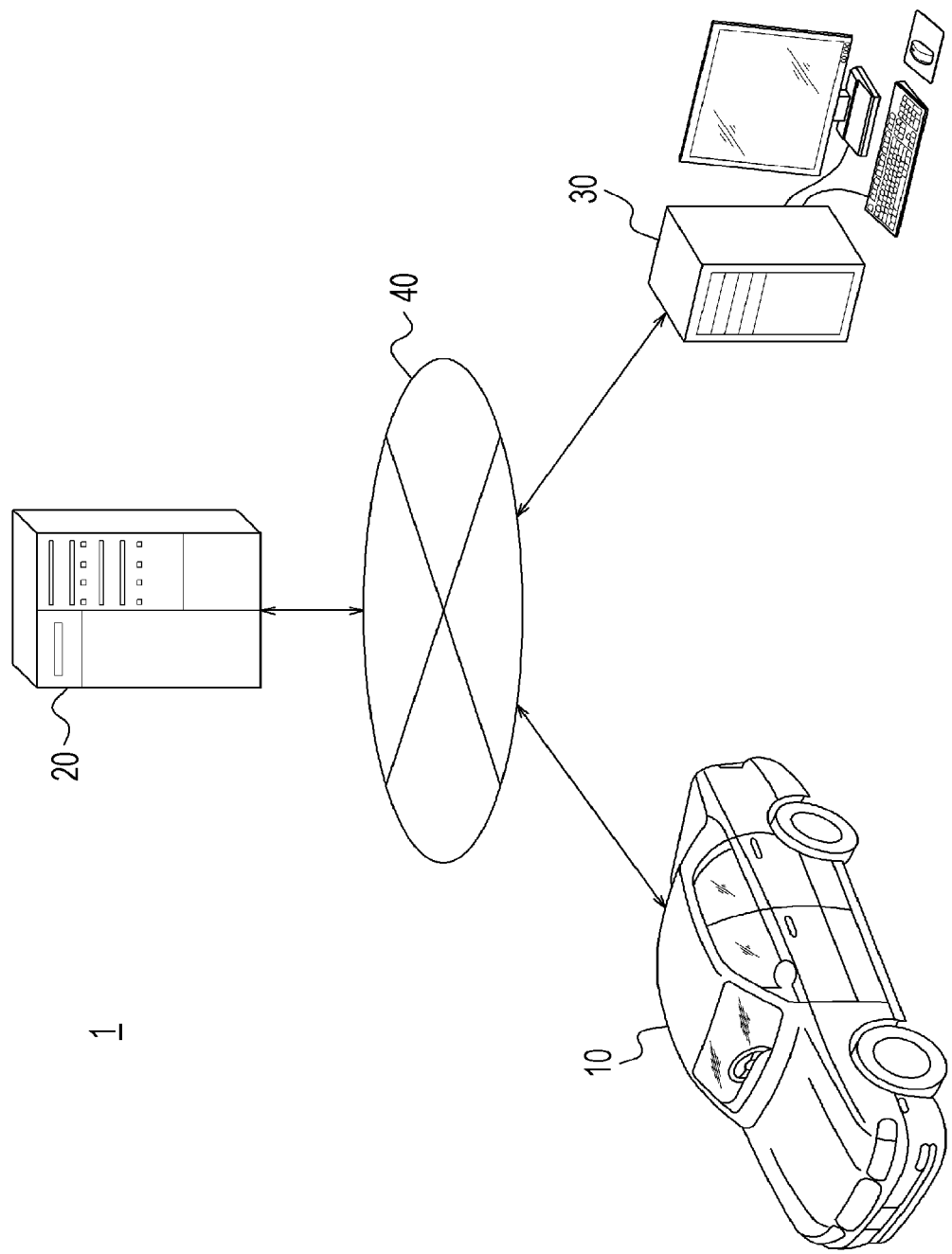
FIG. 1 is a diagram schematically illustrating a configuration of an information processing system according to an embodiment of the disclosure.

Hereinafter, an embodiment of the disclosure will be described with reference to the accompanying drawings.
Information Processing System FIG. 1 is a diagram schematically illustrating a configuration of an information processing system 1 according to an embodiment of the disclosure. The configuration and functions of the information processing system 1 according to an embodiment of the disclosure will be mainly described with reference to FIG. 1.

The information processing system 1 includes a vehicle 10, an information processing device 20, and an information processing terminal 30. The vehicle 10, the information processing device 20, and the information processing terminal 30 are communicatively connected to, for example, a network 40 including a mobile communication network and the Internet. For example, the vehicle 10 and the information processing device 20 are communicatively connected to each other via the network 40. For example, the information processing device 20 and the information processing terminal 30 are communicatively connected to each other via the network 40.

The vehicle 10 is, for example, an automobile, but is not limited thereto and may be an arbitrary vehicle which a person can board. The vehicle 10 is a vehicle which is driven by a driver, but is not limited thereto and may be, for example, a vehicle which is subjected to automated driving. Automated driving includes, for example, levels 1 to 5 which are defined in the Society of Automotive Engineers (SAE), but is not limited thereto and may be arbitrarily defined. In FIG. 1, for the purpose of convenience of explanation, only one vehicle 10 is illustrated, but the number of vehicles 10 in the information processing system 1 is one or more.

The information processing device 20 includes, for example, one server or a plurality of servers which can communicate with each other. The information processing device 20 is not limited thereto and may be an arbitrary general-purpose electronic device such as a personal computer (PC) or a smartphone or may be another electronic device dedicated for the information processing system 1. In FIG. 1, for the purpose of convenience of explanation, only one server constituting the information processing device 20 is illustrated.

The information processing terminal 30 is, for example, a PC which is owned by a travel agency. The information processing terminal 30 is not limited thereto and may be a smartphone of an employee of the travel agency or may be a server which is used by the travel agency. The travel agency is an arbitrary travel agency which acquires tourist attraction information which will be described later and which is generated by the information processing system 1 and which tries to utilize the acquired tourist attraction information in business of the travel agency.

The configuration of the information processing terminal 30 is not limited to the above description. The information processing terminal 30 may be, for example, a PC or a smartphone which is owned by an arbitrary service provider other than a travel agency, an occupant of the vehicle 10, or a general tourist who desires to acquire tourist attraction information generated by the information processing system 1.

In an outline of this embodiment, the information processing device 20 acquires information on an occupant of the vehicle 10 and position information of the vehicle 10 which are acquired by the vehicle 10 from the vehicle 10 via the network 40. An occupant of the vehicle 10 includes a driver and a fellow passenger of the vehicle 10. The number of occupants of the vehicle 10 may be one or may be two or more. When it is determined based on the information on an occupant of the vehicle 10 that the vehicle 10 has traveled to the vicinity of a hidden tourist attraction, the information processing device 20 generates tourist attraction information including the position information of the vehicle 10 at a point P at which such a result of determination has been acquired. The information processing device 20 extracts the position information of the vehicle 10 at the point P with reference to road map information. The road map information may be stored in advance by the information processing device 20 or may be appropriately acquired from an external information processing device.

In this way, according to this embodiment, the information processing system 1 can contribute to discovery of a hidden tourist attraction based on the information on an occupant of the vehicle 10. By causing the information processing system 1 to provide the generated tourist attraction information to, for example, a travel agency, the travel agency can provide a more complete service to clients using the acquired tourist attraction information. For example, the travel agency may introduce a new tourist attraction which has not been recognized as a tourist attraction yet at the time of presenting a travel plan to clients using the tourist attraction information acquired from the information processing system 1.

The elements of the information processing system 1 will be described below in detail.

Vehicle

Figure 2:
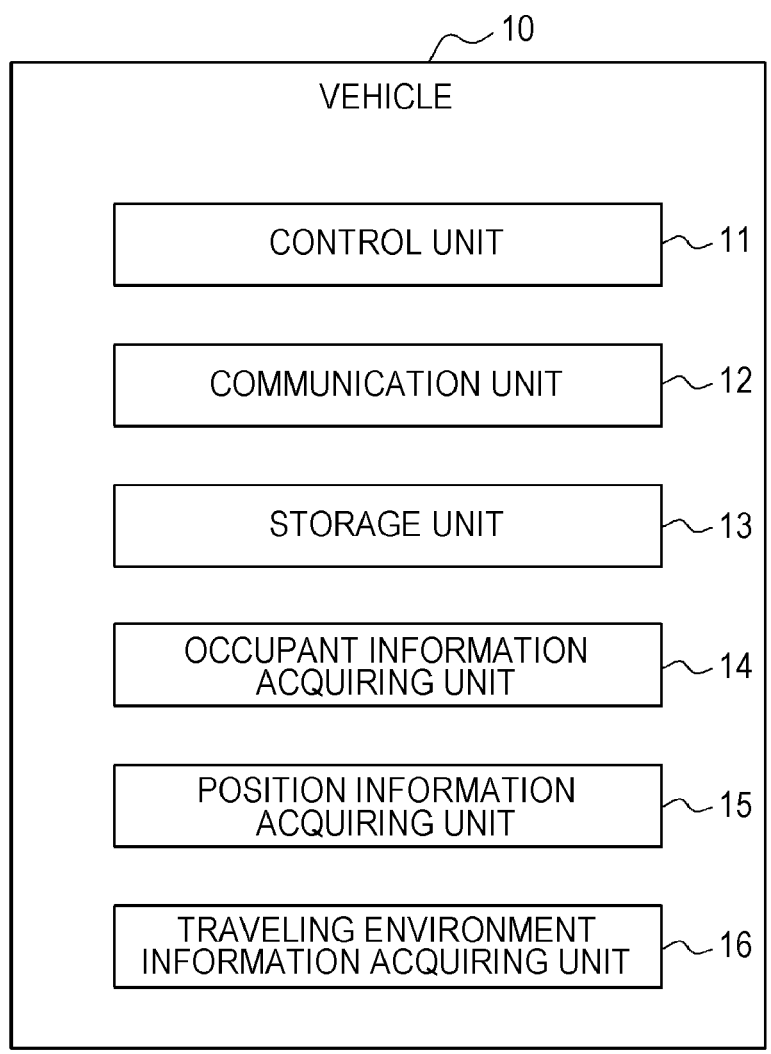
FIG. 2 is a block diagram schematically illustrating a configuration of a vehicle.

FIG. 2 is a block diagram schematically illustrating a configuration of a vehicle 10. As illustrated in FIG. 2, the vehicle 10 includes a control unit 11, a communication unit 12, a storage unit 13, an occupant information acquiring unit 14, a position information acquiring unit 15, and a traveling environment information acquiring unit 16. These constituent units of the vehicle 10 are communicatively connected to each other, for example, via an onboard network such as a controller area network (CAN) or a dedicated line.

The control unit 11 includes one or more processors. In this embodiment, a "processor" is a general-purpose processor or a dedicated processor specialized in a specific process, but is not limited thereto. An electronic control unit (ECU) which is mounted in the vehicle 10 may serve as the control unit 11. For example, the control unit 11 is communicatively connected to the constituent units of the vehicle 10 and controls the entire operation of the vehicle 10. In this embodiment, for example, the control unit 11 acquires a variety of information by controlling the information acquiring units. For example, the control unit 11 controls the communication unit 12 such that the acquired information is transmitted to the information processing device 20 via the network 40.

The communication unit 12 includes a communication module that performs communication via the onboard network or the dedicated line. The communication unit 12 includes a communication module that is connected to the network 40. For example, the communication unit 12 may include a communication module supporting a mobile communication standard such as 4th generation (4G) or 5th generation (5G). For example, an onboard communication device such as a data communication module (DCM) may serve as the communication unit 12. In this embodiment, the vehicle 10 is connected to the network 40 via the communication unit 12.

The storage unit 13 includes one or more memories. In this embodiment, a "memory" may be, for example, a semiconductor memory, a magnetic memory, or an optical memory, but is not limited thereto. Each memory included in the storage unit 13 may serve as, for example, a main storage device, an auxiliary storage device, or a cache storage device. The storage unit 13 stores arbitrary information which is used for operation of the vehicle 10. For example, the storage unit 13 may store a system program, an application program, road traffic information, road map information, and a variety of information which is acquired by the information acquiring units of the vehicle 10. Information stored in the storage unit 13 may be updated, for example, based on information which is acquired from the network 40 via the communication unit 12.

The occupant information acquiring unit 14 acquires information on an occupant in a passenger compartment of the vehicle 10. In this embodiment, the occupant information acquiring unit 14 includes an inside camera that images the passenger compartment of the vehicle 10. The occupant information acquiring unit 14 acquires, for example, information on an occupant from an image which is captured by the inside camera. Here, the information on an occupant includes at least one of attributes including an expression, a face direction, a sight line, a blinking state, an action, and speech and behavior of an occupant of the vehicle 10, the number of occupants, belongings, a driving (boarding) duration time, age, sex, nationality, and race. The occupant information acquiring unit 14 may continually acquire the information on an occupant or may periodically acquire the information on an occupant.

The occupant information acquiring unit 14 may acquire the information on an occupant such as an expression, a face direction, a sight line, and a blinking state of an occupant from an image captured by the inside camera, for example, using a face recognition technique. In addition, the occupant information acquiring unit 14 may acquire the information on an occupant from an image captured by the inside camera using an arbitrary image recognition technique.

The configuration of the occupant information acquiring unit 14 is not limited to the above description. The occupant information acquiring unit 14 may include an arbitrary image sensor other than the inside camera. The occupant information acquiring unit 14 may include another arbitrary sensor which is connected to the CAN.

For example, the occupant information acquiring unit 14 may include an arbitrary sound sensor that is provided in the passenger compartment of the vehicle 10 and is connected to the CAN. The occupant information acquiring unit 14 may acquire the information on an occupant, for example, from output information which is output from the sound sensor. Here, the information on an occupant may include sound information resulting from an occupant, such as conversation details of the occupant, speech generated by an action of an occupant who speaks another spoken language, and sounds generated by an action of an occupant who emits other sounds.

The occupant information acquiring unit 14 may acquire the information on an occupant form the output information output from the sound sensor, for example, using a speech recognition technique and other arbitrary recognition techniques.

For example, the occupant information acquiring unit 14 may include an arbitrary biometric sensor that is provided in the passenger compartment of the vehicle 10 and is connected to the CAN. The occupant information acquiring unit 14 may acquire the information on an occupant, for example, from output information which is output from the biometric sensor. Here, the information on an occupant may include, for example, biological conditions of an occupant including brainwaves, a cerebral blood flow, a blood pressure, a blood sugar level, blood amino acids, a heartbeat, a pulse, a body temperature, a temperature felt, a sense of hunger, and fatigue.

The position information acquiring unit 15 acquires position information of the vehicle 10. In this embodiment, the position information acquiring unit 15 includes one or more receivers corresponding to an arbitrary satellite positioning system. For example, the position information acquiring unit 15 includes a Global Positioning System (GPS) receiver. Here, the position information acquiring unit 15 acquires the position information of the vehicle 10 based on GPS signals. The position information includes, for example, a latitude, longitude, altitude, and a traveling lane position. The position information acquiring unit 15 may continually acquire the position information of the vehicle 10 or may periodically acquire the position information.

The configuration of the position information acquiring unit 15 is not limited to the above description. The position information acquiring unit 15 may include a geomagnetic sensor and an angular acceleration sensor. Here, the position information acquiring unit 15 may acquire a bearing of the vehicle 10, that is, a traveling direction of the vehicle 10.

The traveling environment information acquiring unit 16 acquires information on a traveling environment of the vehicle 10. In this embodiment, the traveling environment information acquiring unit 16 includes an outside camera that captures a traveling image of the vehicle 10. The traveling environment information acquiring unit 16 acquires the information on a traveling environment, for example, from a traveling image captured by the outside camera. Here, the information on a traveling environment includes, for example, visual information which may be correlated with sightseeing such as scenes and shrines and temples, restaurants, and amusement facilities which are constructed to the vicinity of a traveling road. The traveling environment information acquiring unit 16 may continually acquire the information on a traveling environment or may periodically acquire the information on a traveling environment.

The traveling environment information acquiring unit 16 may acquire the information on a traveling environment from a traveling image captured by the outside camera using an arbitrary image recognition technique.

The configuration of the traveling environment information acquiring unit 16 is not limited to the above description. The traveling environment information acquiring unit 16 may include another arbitrary sensor that is connected to the CAN. The sensor may include, for example, an arbitrary image sensor other than the outside camera, an odor sensor, a temperature sensor, a humidity sensor, and a sound sensor. The traveling environment information acquiring unit 16 may acquire the information on a traveling environment, for example, from output information which is output from the sensors. Here, the information on a traveling environment may include, for example, information on smells of nature, a temperature, a humidity, and sounds of nature to the vicinity of the vehicle 10 in addition to the above description.

Information Processing Device

Figure 3:
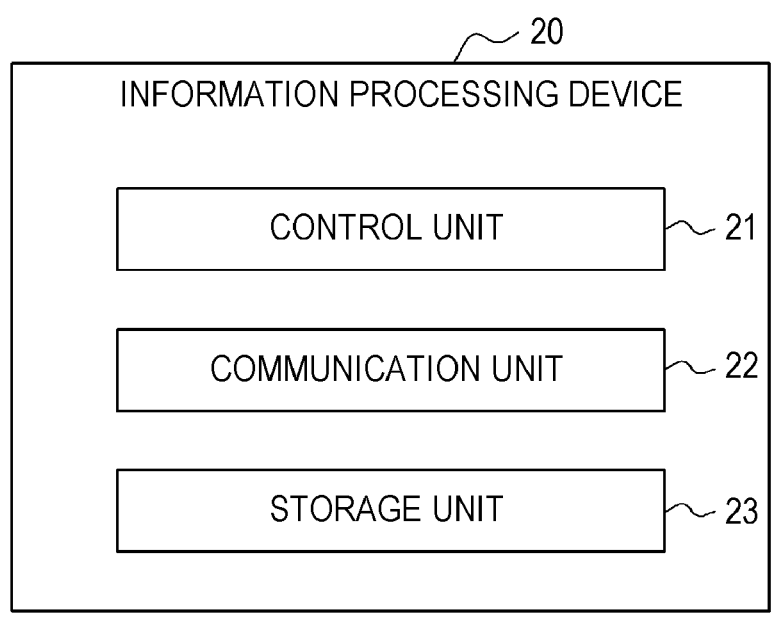
FIG. 3 is a block diagram schematically illustrating a configuration of an information processing device.

FIG. 3 is a block diagram schematically illustrating the configuration of the information processing device 20. As illustrated in FIG. 3, the information processing device 20 includes a control unit 21, a communication unit 22, and a storage unit 23.

The control unit 21 includes one or more processors. The control unit 21 is connected to the constituent units of the information processing device 20 and controls the entire operation of the information processing device 20. For example, the control unit 21 acquires a variety of information from the vehicle 10 via the network 40 by controlling the communication unit 22. For example, the control unit 21 controls the storage unit 23 such that information required for the operation of the information processing system 1 is stored in the storage unit 23.

The communication unit 22 includes a communication module that is connected to the network 40. For example, the communication unit 22 may include a communication module that supports a wired local area network (LAN) standard. In this embodiment, the information processing device 20 is connected to the network 40 via the communication unit 22.

The storage unit 23 includes one or more memories. Each memory included in the storage unit 23 may serve as, for example, a main storage device, an auxiliary storage device, or a cache storage device. The storage unit 23 stores arbitrary information which is used for the operation of the information processing device 20. Information stored in the storage unit 23 may be updated, for example, based on information which is acquired from the network 40 via the communication unit 22. For example, the storage unit 23 may store a system program, an application program, road traffic information, road map information, and a variety of information which is acquired by the information acquiring units of the vehicle 10.

The storage unit 23 stores other information which is required for the operation of the information processing system 1. For example, the storage unit 23 stores determination information for extracting tourist attraction information which is generated by the information processing system 1. The determination information includes position information of a point P at which the control unit 21 determines whether the vehicle 10 has traveled to the vicinity of a hidden tourist attraction. The determination information includes the information on an occupant acquired by the occupant information acquiring unit 14 of the vehicle 10 and a degree of excitement of an occupant in the passenger compartment of the vehicle 10 which will be described later and which is calculated based on the information on an occupant at the point P. The determination information further includes a result of determination which has been performed by the control unit 21. The determination information further includes information on a traveling environment which is acquired by the traveling environment information acquiring unit 16 of the vehicle 10 at the point P. The determination information further includes a traveling direction of the vehicle 10 which is acquired by the position information acquiring unit 15 of the vehicle 10 at the point P. For example, the determination information may be managed as big data by collecting all data when a plurality of vehicles 10 has traveled at a plurality of points P to the information processing device 20.

The control unit 21 determines whether the vehicle 10 has traveled to the vicinity of a hidden tourist attraction based on the information on an occupant acquired by the occupant information acquiring unit 14 of the vehicle 10. The control unit 21 may continually perform this determination or may periodically perform this determination.

The control unit 21 generates the determination information. More specifically, the control unit 21 correlates a variety of information with position information of a point P at which it is determined whether the vehicle 10 has traveled to the vicinity of a hidden tourist attraction. The variety of information includes the information on an occupant, the degree of excitement of an occupant, the result of determination performed by the control unit 21, the information on a traveling environment, and a traveling direction at the point P.

When it is determined that the vehicle 10 has traveled to the vicinity of a hidden tourist attraction, the control unit 21 generates tourist attraction information including the position information of the vehicle 10 at the point P of determination. More specifically, the control unit 21 extracts a variety of information correlated with the point P at which it is determined that the vehicle 10 has traveled to the vicinity of a hidden tourist attraction, for example, out of the determination information which is acquired for a plurality of points P as tourist attraction information.

The control unit 21 calculates a degree of excitement of an occupant in the passenger compartment of the vehicle 10, for example, using machine learning based on the information on an occupant acquired by the occupant information acquiring unit 14 of the vehicle 10. The control unit 21 may have a configuration for an arbitrary learning process to perform such a calculation process. The degree of excitement of an occupant may be calculated based on an arbitrary index. For example, the degree of excitement of an occupant may be expressed by one of three levels including "low," "middle," and "high." The degree of excitement of an occupant may be calculated for each occupant or may be calculated as an average of degrees of excitement of occupants when there is a plurality of occupants.

The control unit 21 determines whether the vehicle 10 has traveled to the vicinity of a hidden tourist attraction based on the calculated degree of excitement of an occupant. For example, the control unit 21 determines that the vehicle 10 has traveled to the vicinity of a hidden tourist attraction when the calculated degree of excitement of an occupant is "high." However, the disclosure is not limited thereto and the control unit 21 may determine that the vehicle 10 has traveled to the vicinity of a hidden tourist attraction when the calculated degree of excitement of an occupant is "high" or "middle." The control unit 21 extracts a variety of information correlated with a point P at which a predetermined degree of excitement of an occupant has been acquired, for example, out of the determination information acquired for a plurality of points P as tourist attraction information. The tourist attraction information includes the degree of excitement of an occupant which is calculated at the point P.

The degree of excitement of an occupant is not limited to the above description. The degree of excitement of an occupant may be expressed by numerical values from 0 to 100. The degree of excitement of an occupant may be expressed by numerical values in an arbitrary numerical range. Here, as the value of the degree of excitement of an occupant increases, it means that an occupant of the vehicle 10 becomes more excited. On the other hand, as the value of the degree of excitement of an occupant decreases, it means that an occupant of the vehicle 10 becomes calmer.

Here, the control unit 21 may compare the calculated degree of excitement of an occupant with a predetermined threshold value and determine whether the vehicle 10 has traveled to the vicinity of a hidden tourist attraction. For example, when the calculated degree of excitement of an occupant is greater than the predetermined threshold value, the control unit 21 may determine that the vehicle 10 has traveled to the vicinity of a hidden tourist attraction. For example, the control unit 21 may extract a variety of information correlated with a point P at which the calculated degree of excitement of an occupant becomes greater than the predetermined threshold value out of the determination information acquired for a plurality of points P as tourist attraction information.

The control unit 21 provides the generated tourist attraction information to, for example, a travel agency. For example, the control unit 21 may transmit the generated tourist attraction information to an information processing terminal 30 of a travel agency via the communication unit 22. For example, the control unit 21 may allow an employee of a travel agency to browse the tourist attraction information stored in the storage unit 23 based on an access to the information processing device 20 via the network 40.

A target to which the control unit 21 provides tourist attraction information is not limited to a travel agency. The control unit 21 may provide the generated tourist attraction information to an arbitrary service provider other than a travel agency or may directly provide the tourist attraction information to an occupant of a vehicle 10 or a general tourist.

FIG. 4 is a diagram illustrating a specific example of determination information including tourist attraction information which is stored in the storage unit 23 of the information processing device 20. The determination information including tourist attraction information which is generated by the information processing system 1 will be more specifically described below with reference to FIG. 4. In FIG. 4, for the purpose of convenience of explanation, only representative points P1, P2, and P3, for example, out of points P at which a plurality of vehicles 10 has traveled are illustrated. However, the disclosure is not limited thereto and the points P at which the vehicles 10 have traveled may include one or more other points other than the points P1, P2, and P3 or may include only one or two of the points P1, P2, and P3.

For example, at the point P1, the occupant information acquiring unit 14 of the vehicle 10 acquires an expression and an action of an occupant who is very excited from an image captured by the inside camera of the vehicle 10. Here, the control unit 21 of the information processing device 20 calculates a degree of excitement of an occupant in the passenger compartment of the vehicle 10 as being "high" based on the acquired information on the occupant. The control unit 21 determines that the vehicle 10 has traveled to the vicinity of a hidden tourist attraction based on the calculated degree of excitement of an occupant. That is, the control unit 21 determines that there is a hidden tourist attraction in the vicinity of the point P1. The traveling environment information acquiring unit 16 of the vehicle 10 acquires a scene at the point P1, for example, from a traveling image captured by the outside camera of the vehicle 10. The position information acquiring unit 15 of the vehicle 10 acquires a traveling direction of the vehicle 10 which is, for example, "north" at the point P1.

For example, at the point P2, the occupant information acquiring unit 14 of the vehicle 10 acquires an expression and an action of an occupant who is slightly excited from an image captured by the inside camera of the vehicle 10. Here, the control unit 21 of the information processing device 20 calculates a degree of excitement of an occupant in the passenger compartment of the vehicle 10 as being "middle" based on the acquired information on the occupant. The control unit 21 determines that the vehicle 10 has not traveled to the vicinity of a hidden tourist attraction based on the calculated degree of excitement of an occupant. That is, the control unit 21 determines that there is no hidden tourist attraction in the vicinity of the point P2. The traveling environment information acquiring unit 16 of the vehicle 10 acquires sounds of nature at the point P2, for example, from output information which is output from a sound sensor of the vehicle 10. The position information acquiring unit 15 of the vehicle 10 acquires a traveling direction of the vehicle 10 which is, for example, "south" at the point P2.

For example, at the point P3, the occupant information acquiring unit 14 of the vehicle 10 acquires an expression and an action of an occupant who is cool from an image captured by the inside camera of the vehicle 10. Here, the control unit 21 of the information processing device 20 calculates a degree of excitement of an occupant in the passenger compartment of the vehicle 10 as being "low" based on the acquired information on the occupant. The control unit 21 determines that the vehicle 10 has not traveled to the vicinity of a hidden tourist attraction based on the calculated degree of excitement of an occupant. That is, the control unit 21 determines that there is no hidden tourist attraction in the vicinity of the point P3. The traveling environment information acquiring unit 16 of the vehicle 10 acquires smells of nature at the point P3, for example, from output information which is output from an odor sensor of the vehicle 10. The position information acquiring unit 15 of the vehicle 10 acquires a traveling direction of the vehicle 10 which is, for example, "east" at the point P3.

The control unit 21 of the information processing device 20 extracts a variety of information correlated with the point P1 at which calculated degree of excitement of an occupant is "high" and it is determined that there is a hidden tourist attraction near as tourist attraction information out of the determination information. More specifically, the extracted tourist attraction information includes the information on an occupant, the degree of excitement of an occupant, the result of determination for a hidden tourist attraction, the information on a traveling environment, and the traveling direction which are correlated with the position information of the point P1.

Operation Flow of Information Processing System

FIG. 5 is a sequence diagram illustrating an example of an operation flow in the information processing system 1. An example of the operation flow in the information processing system 1 will be described below with reference to FIG. 5.

Step S100: The control unit 11 of the vehicle 10 acquires position information and a traveling direction of the vehicle 10 using the position information acquiring unit 15. The control unit 11 of the vehicle 10 acquires information on an occupant in the passenger compartment of the vehicle 10 using the occupant information acquiring unit 14. The control unit 11 of the vehicle 10 acquires information on a traveling environment of the vehicle 10 using the traveling environment information acquiring unit 16.

Step S101: The control unit 11 of the vehicle 10 transmits the position information, the traveling direction, the information on an occupant, and the information on a traveling environment of the vehicle 10 which are acquired in Step S100 to the information processing device 20 using the communication unit 12. For example, the control unit 21 of the information processing device 20 may continually acquire the position information, the traveling direction, the information on an occupant, and the information on a traveling environment of the vehicle 10 from the communication unit 12 or may acquire such information at an appropriate time.

Step S102: The control unit 21 of the information processing device 20 calculates a degree of excitement of an occupant in the passenger compartment of the vehicle 10 based on the information on an occupant which is acquired in Step S100.

Step S103: The control unit 21 of the information processing device 20 determines whether the vehicle 10 has traveled to the vicinity of a hidden tourist attraction based on the degree of excitement of an occupant which is calculated in Step S102.

Step S104: The control unit 21 of the information processing device 20 determines that the vehicle 10 has traveled to the vicinity of a hidden tourist attraction.

Step S105: When it is determined in Step S104 that the vehicle 10 has traveled to the vicinity of a hidden tourist attraction, the control unit 21 of the information processing device 20 generates tourist attraction information including the position information of the vehicle 10 at a point P at which the determination has been performed.

Step S106: The control unit 21 of the information processing device 20 transmits the tourist attraction information which is generated in Step S105 to an information processing terminal 30 of a travel agency.

As described above, with the information processing system 1 according to this embodiment, it is possible to contribute to discovery of a hidden tourist attraction based on information on an occupant of a vehicle 10. By causing the control unit 21 of the information processing system 1 to transmit the generated tourist attraction information, for example, to an information processing terminal 30 of a travel agency, the travel agency can provide a more complete service to clients using the acquired tourist attraction information. For example, the travel agency may introduce a new tourist attraction which has not been recognized yet as a tourist attraction to clients at the time of presenting a travel plan to the clients using the tourist attraction information acquired from the information processing system 1. Accordingly, the travel agency can call clients' attention to demand for travel. Similarly, an arbitrary service provider other than a travel agency can use the tourist attraction information acquired from the information processing system 1 to correspond to a service which is provided by the arbitrary service provider. For example, when drive or travel is planned, an occupant of a vehicle 10 and a general tourist may prepare a new drive route and a travel plan including a new tourist attraction with reference to the tourist attraction information acquired from the information processing system 1.

Since the information processing system 1 calculates a degree of excitement of an occupant at a point P based on information on an occupant, the information processing system 1 can acquire a reaction of an occupant of the vehicle 10 at the point P as more objective information. Accordingly, the information processing system 1 can more accurately determine whether the vehicle 10 has traveled to the vicinity of a hidden tourist attraction.

Since tourist attraction information includes a degree of excitement of an occupant calculated at a point P, a target company or a target person to whom tourist attraction information is provided from the information processing system 1 can apply the tourist attraction information to a service thereof or apply the tourist attraction information to preparation of a drive route or a travel plan with reference to the degree of excitement of an occupant of the vehicle 10 at the point P. For example, when the tourist attraction information includes position information of a plurality of points P and different degrees of excitement of an occupant are correlated with the points P, a target company or a target person to whom tourist attraction information is provided may rank degrees of attractiveness at the points P as a new tourist attraction based on the degree of excitement of an occupant.

Since tourist attraction information includes information on a traveling environment which is acquired at a point P, a target company or a target person to whom the tourist attraction information is provided from the information processing system 1 can apply the tourist attraction information to a service thereof or apply the tourist attraction information to preparation of a drive route or a travel plan with reference to the information on a traveling environment at the point P together. For example, when the tourist attraction information includes position information of a plurality of points P and different information on a traveling environment is correlated with the points P, a target company or a target person to whom tourist attraction information is provided may select a point P which is suitable for the type of information on a desired traveling environment. For example, when a travel agency desires to present a point with a good scene as a travel plan to a client, the travel agency can select tourist attraction information at a point P which is correlated with a scene as the information on a traveling environment. For example, when an occupant of a vehicle 10 or a general tourist wants to enjoy sounds or smells of nature, the occupant or the general tourist can select tourist attraction information at a point P which is correlated with sounds or smells of nature as the information on a traveling environment.

Since the information processing system 1 acquires information on a traveling environment from a traveling image which is captured by an outside camera, the information processing system 1 can acquire information on a traveling environment at a point P based on visual information. Accordingly, the information processing system 1 can add the information on a traveling environment at the point P as visual information to the tourist attraction information. Accordingly, the information processing system 1 can provide tourist attraction information with a sense of reality as visual information to a target company or a target person.

Since tourist attraction information includes a traveling direction of a vehicle 10 which is acquired at a point P, a target company or a target person to whom the tourist attraction information is provided from the information processing system 1 can ascertain an optimal traveling direction in which a high degree of excitement is acquired at the point P in addition to an optimal route to the point P. The information processing system 1 may generate information on the optimal route to the point P and the optimal traveling direction at the point P in combination with or in addition to the tourist attraction information and provide the generated information to a target company or a target person.

Since the information processing system 1 transmits tourist attraction information to the information processing terminal 30, it is possible to enhance convenience for a target company or a target person to whom the tourist attraction information is provided from the information processing system 1. A target company or a target person can easily acquire the tourist attraction information at a point P without accessing the information processing device 20.

The information processing system 1 can acquire information on an occupant at a point P based on visual information by acquiring the information on an occupant from an image which is acquired by the inside camera. Accordingly, the information processing system 1 can add the information on an occupant at the point P as visual information to the tourist attraction information and provide the result information to a target company or a target person. A target company or a target person can visually ascertain a reaction of an occupant of the vehicle 10 at the point P based on the information on an occupant acquired as visual information from the information processing system 1.

The information processing system 1 can acquire a variety of information on an occupant which cannot be acquired based on visual information by acquiring information on an occupant of a vehicle 10 from output information which is output from an arbitrary sensor that can acquire information on an occupant. For example, the information processing system 1 can acquire sound information resulting from an occupant which cannot be acquired based on visual information from output information which is output from a sound sensor. For example, the information processing system 1 can acquire delicate change in emotion which cannot be acquired based on visual information as biometric conditions of an occupant from output information which is output from a biometric sensor.

While the disclosure has been described above in conjunction with all the drawings and the embodiment, it should be noted by those skilled in the art that various modifications and corrections can be easily made based on the present disclosure. Accordingly, it should be noted that such modifications and corrections are included in the scope of the disclosure. For example, the functions included in the units or the operations can be rearranged as long as doing so does not result in logical inconsistency, and a plurality of units or operations may be combined into one unit or an operation or may be divided.

For example, in the above-mentioned embodiment, the constituent units of the vehicle 10 are mounted in the vehicle 10. However, some or all processing operations which are performed by the constituent units of the vehicle 10 may be performed by an arbitrary electronic device such as a smartphone or a computer.

For example, a general-purpose electronic device such as a smartphone or a computer may be made to serve as the constituent units of the vehicle 10 or the information processing device 20 according to the above-mentioned embodiment. For example, a program in which processing details for realizing the functions of the communication unit 12 and the like according to the embodiment are described may be stored in a memory of an electronic device and a processor of the electronic device may be made to read and execute the program. Accordingly, the embodiment of the disclosure can also be embodied as a program which can be executed by a processor.

In the above-mentioned embodiment, the vehicle 10 and the information processing device 20 are communicatively connected to each other via the network 40. However, a configuration in which the information processing device 20 is mounted in the vehicle 10 and directly acquires information acquired by the vehicle 10 from the vehicle 10 without using the network 40 may be employed. That is, a configuration in which the vehicle 10 and the information processing device 20 transmit and receive information directly without using the network 40 may be employed.

Here, similar to the above-mentioned embodiment, the control unit 11 and the control unit 21 may be constituted by different processors and be separately provided in the vehicle 10 and the information processing device 20. Unlike the above-mentioned embodiment, the control unit 11 and the control unit 21 may be constituted by the same processor and be configured as a single control unit which is included in both the vehicle 10 and the information processing device 20. That is, processing operations of the vehicle 10 and the information processing device 20 may be realized by a single control unit.

In the above-mentioned embodiment, tourist attraction information which is generated by the information processing system 1 includes position information of a point P, information on an occupant, a degree of excitement of an occupant, a result of determination on a hidden tourist attraction, information on a traveling environment, and a traveling direction, but is not limited thereto. The tourist attraction information has only to include at least position information of a point P and may or may not further include other information.

In the above-mentioned embodiment, the control unit 21 determines whether a vehicle 10 has traveled to the vicinity of a hidden tourist attraction based on a degree of excitement of an occupant. However, the disclosure is not limited thereto and the control unit 21 may not calculate a degree of excitement of an occupant and determine that the vehicle 10 has traveled to the vicinity of a hidden tourist attraction when predetermined information on an occupant is acquired. The predetermined information on an occupant may include, for example, a predetermined action of an occupant such as pointing forward while turning a slight line to the outside of the vehicle, predetermined conversation details such as "beautiful scene" which is uttered by an occupant, and a predetermined biometric condition such as a specific brain-wave pattern.

In the above-mentioned embodiment, the information processing system 1 calculates a degree of excitement of an occupant at a point P based on information on an occupant. However, information which is calculated based on the information on an occupant is not limited to a degree of excitement of an occupant at the point P. Information which is calculated based on the information on an occupant may be an arbitrary index which is correlated with an occupant's reaction including a degree of favorable impression, a degree of surprise, and a degree of impression of an occupant at the point P.

In the above-mentioned embodiment, determination information including tourist attraction information is managed as big data by collecting all data when a plurality of vehicles 10 has traveled at a plurality of points P to the information processing device 20. However, the disclosure is not limited thereto and determination information including tourist attraction information may be managed as data when at least one vehicle 10 has traveled through at least one point P.

What is claimed is:

1. An information processing system comprising:
a vehicle; and
a processor configured to acquire information acquired by the vehicle from the vehicle,
wherein the vehicle is configured to
acquire information on an occupant in a passenger compartment of the vehicle,
acquire position information of the vehicle,
acquire a traveling direction of the vehicle, and
acquire information on a traveling environment of the vehicle, and
wherein the processor is configured to
calculate a degree of excitement of the occupant in the passenger compartment of the vehicle based on the information on the occupant, the degree of excitement being expressed by one of three levels or a numerical value in a numerical range,
determine whether the vehicle has traveled to the vicinity of a hidden tourist attraction based on the degree of excitement of the occupant,
when determining based on the degree of excitement of the occupant that the vehicle has traveled to the vicinity of the hidden tourist attraction, generate tourist attraction information including the position information of the vehicle, the traveling direction of the vehicle that are acquired at a point at which the determination has been performed, the information on the traveling environment acquired at the point, and the information on the traveling environment includes information on smells of nature, a temperature, a humidity, and sounds of nature, and
transmit the tourist attraction information to an information processing terminal of a travel agency.

2. The information processing system according to claim 1, wherein the tourist attraction information further includes the degree of excitement of the occupant which is calculated at the point.

3. The information processing system according to claim 1, wherein the vehicle includes an outside camera that captures a traveling image of the vehicle and is configured to acquire information on the traveling environment from the traveling image captured by the outside camera.

4. The information processing system according to claim 1, wherein the vehicle includes an inside camera that images the passenger compartment in the vehicle and is configured to acquire the information on the occupant from an image captured by the inside camera.

5. The information processing system according to claim 1, wherein the processor is configured to determine whether the vehicle has traveled to the vicinity of the hidden tourist attraction when the degree of excitement is greater than a predetermined threshold value.

6. A non-transitory storage medium storing a program that operates in an information processing system including a vehicle and a processor configured to acquire information acquired by the vehicle from the vehicle, the program causing the vehicle to perform:
    acquiring information on an occupant in a passenger compartment of the vehicle;
    acquiring position information of the vehicle;
    acquiring a traveling direction of the vehicle; and
    acquiring information on a traveling environment of the vehicle, and the program causing the processor to perform:
    calculating a degree of excitement of the occupant in the passenger compartment of the vehicle based on the information on the occupant, the degree of excitement being expressed by one of three levels or a numerical value in a numerical range;
    determining whether the vehicle has traveled to the vicinity of a hidden tourist attraction based on the degree of excitement of the occupant;
    when the processor determines that the vehicle has traveled to the vicinity of the hidden tourist attraction, generating tourist attraction information including the position information of the vehicle, the traveling direction of the vehicle that are acquired at a point at which the determination has been performed, the information on the traveling environment acquired at the point, and the information on the traveling environment includes information on smells of nature, a temperature, a humidity, and sounds of nature; and
    transmitting the tourist attraction information to an information processing terminal of a travel agency.

7. The non-transitory storage medium according to claim 6, wherein the program causes the processor to perform determining whether the vehicle has traveled to the vicinity of the hidden tourist attraction when the degree of excitement is greater than a predetermined threshold value.

8. A control method in an information processing system including a vehicle and a processor configured to acquire information acquired by the vehicle from the vehicle, the control method comprising:
    causing the vehicle to acquire information on an occupant in a passenger compartment of the vehicle;
    causing the vehicle to acquire position information of the vehicle;
    causing the vehicle to acquire a traveling direction of the vehicle;
    causing the vehicle to acquire information on a traveling environment of the vehicle;
    causing the processor to calculate a degree of excitement of the occupant in the passenger compartment of the vehicle based on the information on the occupant, the degree of excitement being expressed by one of three levels or a numerical value in a numerical range;
    causing the processor to determine whether the vehicle has traveled to the vicinity of a hidden tourist attraction based on the degree of excitement of the occupant;
    when the processor determines that the vehicle has traveled to the vicinity of the hidden tourist attraction, causing the processor to generate tourist attraction information including the position information of the vehicle, the traveling direction of the vehicle that are acquired at a point at which the determination has been performed, the information on the traveling environment acquired at the point, and the information on the traveling environment includes information on smells of nature, a temperature, a humidity, and sounds of nature, and
    causing the processor to transmit the tourist attraction information to an information processing terminal of a travel agency.

9. The control method according to claim 8, wherein the processor is caused to determine whether the vehicle has traveled to the vicinity of the hidden tourist attraction when the degree of excitement is greater than a predetermined threshold value.

* * * * *